United States Patent
Lee et al.

(10) Patent No.: US 8,565,869 B2
(45) Date of Patent: Oct. 22, 2013

(54) DEVICE AND SYSTEM TO IMPROVE THE SAFETY OF AN ELECTRICAL STIMULATING DEVICE IN AN ELECTROMAGNETIC RADIATION ENVIRONMENT

(76) Inventors: Chong Il Lee, Stanton, CA (US); Sergio Lara Pereira Monteiro, Los Angeles, CA (US)

( * ) Notice: Subject to any disclaimer, the term of this patent is extended or adjusted under 35 U.S.C. 154(b) by 20 days.

(21) Appl. No.: 13/046,801

(22) Filed: Mar. 14, 2011

(65) Prior Publication Data
US 2011/0276101 A1 Nov. 10, 2011

Related U.S. Application Data

(60) Provisional application No. 61/340,183, filed on Mar. 15, 2010.

(51) Int. Cl.
*A61N 1/08* (2006.01)

(52) U.S. Cl.
USPC .............................................. 607/2

(58) Field of Classification Search
USPC .............................................. 607/2
See application file for complete search history.

(56) References Cited

U.S. PATENT DOCUMENTS

2005/0043761 A1* 2/2005 Connelly et al. ............. 607/2
2012/0130452 A1* 5/2012 Inman et al. ................ 607/62

* cited by examiner

*Primary Examiner* — Christopher D Koharski
*Assistant Examiner* — Frances Oropeza (57) ABSTRACT

A device to improve the safety of neuronal, heart, muscle and organ electrical stimulation devices during MRI scanning. The device consists of means to open and/or closing the circuit to the electrical stimulation device and to the battery pack, while, concomitantly, closing and/or opening another circuit to a dedicated path that dissipates the stored energy induced by the radiofrequency used in imaging MRI.

18 Claims, 4 Drawing Sheets

DEVICE AND SYSTEM TO IMPROVE THE SAFETY OF AN ELECTRICAL STIMULATING DEVICE IN AN ELECTROMAGNETIC RADIATION ENVIRONMENT

CROSS REFERENCE TO RELATED APPLICATIONS

This application claims the benefit of Provisional Application Ser. No. 61/340,183, entitled "Device and means to obstruct propagation of electromagnetic radiation in implanted body electrodes" filed Mar. 15, 2010, by the present inventors which is incorporated herein by reference in its entirety. This patent is related to patent application Ser. Nos. 12/586,562, filed 24 Sep. 2009, now partly issued under U.S. Pat. No. 8,335,551, and Ser. No. 12/586,763, filed Sep. 28, 2009, all by the present inventors.

BACKGROUND OF THE INVENTION

This invention relates to electrical stimulation of animal cells, particularly human brain and heart electrical stimulation, including spine and other types of neurons, other types of muscles and organs like bladder and stomach, and in particular to the possibility of partial obstruction of the current induced in same by electromagnetic radiation, e.g., induced during MRI (Magnetic Resonance Imaging).

In the body of this patent we will be using the word "radiation", which is a widely used term with many meanings, here used as EM (electromagnetic) radiation only. Note that "radiation" is often used as a short for "ionizing radiation", as gamma rays, which can cause cancer. The frequencies used in our case are non-ionizing, so radiation used in this context is not cancer-causing agent.

Telemetry, used in the context of implanted devices for DBS, means the transmission of information using EM waves or any similar action-at-a-distance physical phenomenon, to send instructions to modify the state of operation of the device. Typically the instructions are send to the microcontroller embedded in the battery/electronics pack located in the chest, but nothing forbids other receiving units in other locations.

Several types of implanted devices for the purpose of delivering electrical pulses to different parts of the body have become practical, the most ubiquitous of which being the cardiac pacemaker, but also including DBS (Deep Brain Stimulation) and other neuronal stimulating devices, as for pain control, and other stimulators in the brain and peripheral nervous system as well, and also for other needs, as bowl control and the like. One of the disadvantages of wearing some of these, is their propensity to absorb electromagnetic waves (EM waves), which are induced AC, which is subsequently released as heat in localized spots in the wearer's body, with potential for discomfort, pain, or worse, depending on the temperature increase, or electrical interference with normal neural signals. In heart pacemakers another type of danger exists, which is the transfer of induced voltage on the connecting wires to the heart, or worse, to the heart sinus pacemaker, which could induce unwanted and erratic heart beats with the potential of causing the heart to stop. In other words, the wirings act as an antenna that then is the origin of current pulses along the device. The danger also exists to totally or partly destroy the electronic circuit that controls the device if the electromagnetic induced (EM induced) AC propagates to it, with the potential of erratic electrical pulses, with unpredictable consequences, including death too. These implanted devices are generally composed of a battery and an electronic circuit, which is implanted near the skin, for easy access if a need arises for replacement, from where wires run to the desired electrical stimulation location, as heart, brain, spinal cord, etc. Unfortunately the connecting wires act as antennae for external electromagnetic radiation, which in turn cause an unwanted current to flow through the connecting wire, that ultimately may cause either battery or electronic circuit failure, if the pulse propagates towards the battery, or it may cause heating on the other extremity of the connecting wire, which may then be on or near the heart, brain, spinal cord, etc, wherever the stimulation happens to be. This problem may be especially acute in DBS, because the wires are longer, running from the chest to the top of the skull then down from the top, inside the skull to the bottom of the brain, making DBS a longer antenna for electromagnetic radiation than heart pacemakers are, which in turn causes more energy to be absorbed by the DBS than by the heart pacemakers. With heart pacemakers, on the other hand, though the wires are shorter, so the induced voltage is lower (also the induced energy), the very nature of the device, to pace the heart, with electrodes placed at the most efficient positions to influence the heart beat, any electrical induced voltage is potentially mortally dangerous because it can cause erratic heart beating.

Because of this possible danger, MRI images are often, or at least occasionally, avoided in patients that wear one of these implanted devices, particularly in DBS and heart pacemakers wearers, because of the longer wires on the former, and the rhythmic sensitivity of the latter. DBS wearers carry a longer antenna, from the battery/electronics in the chest with a wire running to the top of the head. Pacemakers, though having shorter wires, are less likely to develop higher power to cause dangerous heating but suffer from the danger of causing heart arrhythmias. This avoidance is a problem because implanted patients are exactly the older ones, which are the ones more likely to need imaging, X-Ray, MRI, sonography, etc. From these, MRI is the worse, because it subjects the patient to a radio frequency (RF), AC electromagnetic field (EM field or EMF) of frequency on the order of 50 MHz, a frequency range used by many communications devices exactly because the antennae are so effective in this range. Because of this, at the very least the medical practitioners are prone to avoid requesting an MRI imaging on patients wearing electrical stimulating implants, particularly on a DBS wearer, who is known to be implanted with a longer wire, more prone to absorb electromagnetic energy created by the MRI imaging system.

This problem is widely recognized in the literature, and much time has been devoted to its solution, yet a complete and inexpensive solution has been eluding the designers of electrical stimulating devices.

Mark Kroll et al. U.S. Pat. No. 7,369,898, May 6, 2008, recognizes the problem and teaches a method to prevent the controlling unit from being disturbed by the RF and then sending erratic stimulating pulses to the stimulation site that are not programmed in the device. Though this is an improvement, it still fails to even address the other problem of induced RF in the conducting wire that goes from the power pack box to the stimulation site. It is only a partial solution. Moreover, Kroll teaches a method that depends on the device itself recognizing the presence of strong magnetic field, then the presence of an RF, before it enters in a self-protective mode. This has the disadvantage of relying on an automatic response, which can fail to activate, as opposed to a human activated response, which can be checked by a trained professional. Above all, Kroll's solution, when and if it succeeds, is a protection for the battery and electronics package only, located in the patient chest, but not a solution for heating and unwanted electrical stimulation due to induced currents in the connecting wires. Indeed, the very solution proposed by Kroll indicates that though the community is aware of the problem and have been trying to solve it for a long time, the true solution has been eluding all, indicating the importance of an inventive, a creative solution for this problem.

Zeijlemaker et al. (U.S. Pat. No. 7,623,930, Nov. 24, 2009) discloses a coordination between the telemetry system and the MRI system with the view of minimizing the possible damage, but it fails to stop the current flow due to induced electromagnetic waves in the wires that comprise the implant device. It also points to the eagerness of the community to solve a serious problem that has been eluding the practitioners of the art.

These examples show that this is a crowded field, with many practitioners of the art trying to solve a serious problem associated with electrical implants interaction with the RF electromagnetic waves used in MRI imaging. Yet, in spite of so much search and resources through in the problem, its solution has been eluding all.

OBJECTS AND ADVANTAGES

Accordingly, several objects and advantages of my invention are:

1. To allow patients wearing electrically implanted devices to receive MRI imaging with a smaller risk of complications arising from the procedure, 2. To decrease the level of worries by treating physician about possible complications from MRI imaging in implanted patients, therefore opening more options for his diagnostics and creating the possibility of better, more professional and accurate diagnostics, 3. To increase the possibility that a patient wearing an electrical stimulation device will indeed have an MRI examination when one is needed for decisions on his/her health,

BRIEF SUMMARY OF THE INVENTION

We claim a method and means to substantially decrease the electric current induced in implanted devices, as, for example, by magnetic resonance imaging (MRI) radio frequency (RF) electromagnetic (EM) radiation from propagating through the wires of electrical devices implanted in patients subjected to MRI imaging or other electromagnetic radiation. Without such blocking, or filter, physicians are at least uneasy about requesting MRI imaging in patients wearing such implants, resulting in diminished information for treatment, at most unable to get an MRI imaging. In the worst case an imaging may cause localized heating and possibly catastrophic results, including death, or erratic heart beating, also with the possibility of death. Our device ameliorates this situation, substantially decreasing the probability that adverse side effects occurs.

DETAILED DESCRIPTION OF THE INVENTION

Preferred Embodiment

Figure 1A:
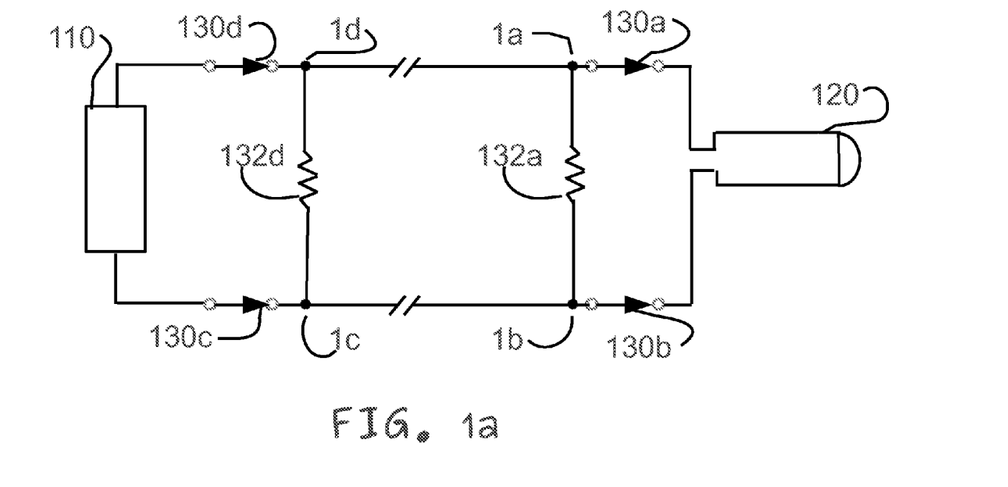
FIG. 1 shows a schematic representation of the implementation of the main embodiment of this invention.
Figure 1B:
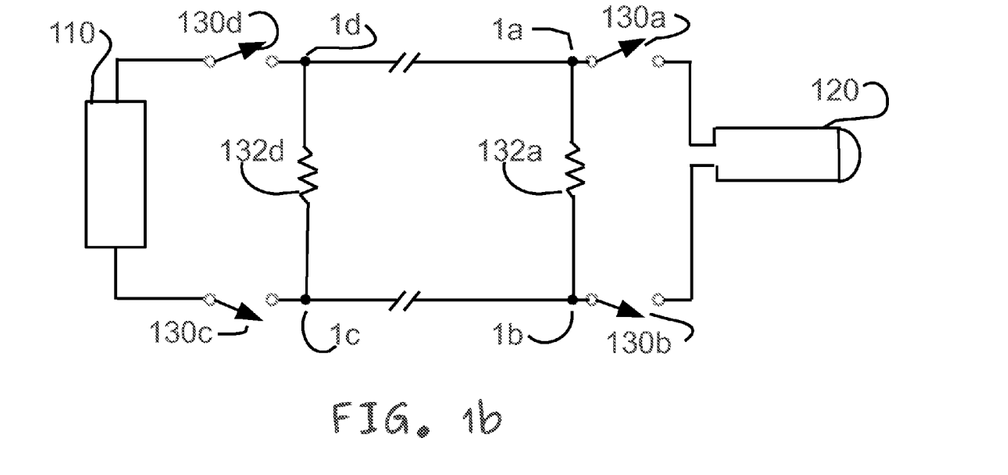

FIGS. 1a and 1b

We start with a shorter detailed description suitable for electronics engineers, followed by a more detailed description with less technical terms for medical personnel and general background readers. Such an approach is useful for the complete description of an invention that is of interest of practitioners of two very different fields: electronics and medicine. The first, technical description, is written for the electrical engineer, the latter, general description, is intended for neurosurgeons, neurologists, medical personnel and anyone without knowledge of the electronics circuits and electrical phenomena.

Detailed Description for Electronics Engineers.

In its main embodiment, the improvement of our invention over prior art electrical stimulating devices, is the introduction of isolation switches (in-line) to prevent propagation of RF electromagnetic waves into the critical parts of the implant, together with alternate path (or paths) in parallel with both the stimulation device (120) and the battery/electronics (110) which serve to damp the electromagnetic energy induced in the connecting wires. It is of note that without the alternate path to form a closed circuit with most of the connecting wire, opening a switch leading to the stimulating device (120) or to the battery/electronics box (110) is likely to cause electric potential increase at the gap with a consequent spark and destruction of the switch. The alternative paths to dump the unavoidable induced EM wave that necessarily is induced in the existing wires is an integral part of the invention we disclose. The latter (the bypass network) are necessary to forestall the destruction of the former (the in-line switches) due to the fast increase in voltage at the switch gap, though our invention is not dependent on any theory that explains the mechanism of destruction, which is added here only for completeness.

Electrical stimulating devices can be generally seen as three main components, but this arbitrary division is made here as only a simplifying subdivision to drive the attention to the parts that are important for the invention. The first component is a battery and other electrical energy source and the controlling electronics (110), which are usually together in a sealed box implanted in the patient's chest, near the skin for easier access; the second are the stimulating electrodes (120), which are made in any necessary shape appropriate for the situation, which for the main embodiment we are considering to be a DBS (Deep Brain Stimulator); and finally, the third component are the wires connecting the former to the latter.

Referring to FIG. 1 (*a* and *b*), the reader can see switches 130*c* and 130*d* which are near the battery pack 110 and switches 130*a* and 130*b*, which are near the stimulating electrodes, which in this case are brain stimulating electrodes, as used in DBS (Deep Brain Stimulation), as an example only, the principle being valid for other electrical stimulation as well. Note that switches 130 (*a*, *b*, *c*, and *d*) allow current to flow into and out of the stimulating device (FIG. 1*a*), or interrupt its flow (FIG. 1*b*). Switches 130 (*a*, *b*, *c*, and *d*) are controlled by telemetry, either directly, or indirectly via commands received from the electronics command unit in 110, which receives commands by telemetry. The telemetry control is made with specially designed equipment that can be controlled either by the patient himself or by a neurologist, a nurse, or any other medically trained person. The electronics for this is not shown in the drawings, it being standard technology in use in many other applications. In particular existing DBS, heart pacemakers and the like do use telemetry devices to adjust the parameters of the stimulating electrical pulse, so the telemetry part is old art, not part of our invention. Our device uses additional commands not used by existing art, say, to open/close 130, but these are obvious extensions for the people with experience in the arts of software and/or digital hardware design, so they will not be discussed here. It is worth to point out that current art of DBS use telemetry to select the parameters appropriate to each patient, as voltage level, for example. A trained person, capable of acting on the controls of the device, is able, using some telemetry control, to turn the switches on and off as needed.

In the main embodiment these switches are semiconductor switches activated by an electronics circuit which contains some logic and perhaps some digital addressing too. Consequently each of the switches needs to be connected to an electrical power. The main embodiment of our invention works with 130 of the type known as normally open switches: without power they go into the open state. To turn all off, the 110 command unit has only to turn 130*c* and 130*d* off, which automatically turns off 130*a* and 130*b* because they lose power. Persons with knowledge in the art of electronics are aware that normally-open switches are not the only possible option, normally-closed switches being also possible, as well as mechanical switches, three-state switches, and more. A semiconductor, normally-open switch is suggested here only as a concrete case, it not being our intention to limit our invention to this option.

Referring still to FIGS. 1*a* and 1*b*, resistances 132*a* and 132*d* are to provide and alternative path to the induced current in the wires after switches 130 (*a, b, c* and *d*) are opened. 132*a* and 132*d* can be considered as a resistive load for the isolated network. The value of the resistances 132*a* and 132*d* are such that their impedances (resistances) is much larger than the total impedance from 130*a* to 130*b* through the network branch that includes the stimulating device, that is, the total impedance from a through 130*a*, the wire connecting 130*a* to the stimulating device 120, the impedance of 120, the impedance of the wire that connects this latter to 130*b*, and finally the impedance of 130*b*. Saying it in other words, the value of the resistance 132*a* is much larger than the total value of the impedance in parallel with 132*a* which contains the stimulating device 120. For the main embodiment 120 is a Deep Brain Stimulating (DBS) device, which has a typical impedance of Z-sub-120=1 k-Ohms, in which case 132*a* should have a resistance 132*a*=1000 k-Ohms=1 M-Ohms. Considering that Joule's law for resistive devices, $$P = V^2/R,$$

states that for a fixed potential difference the dissipated power is inversely proportional to the resistance, with these recommended values the power dissipated in 132*a* would be 1/1000, or 0.1% of the total power dissipated in 120, which is negligible. In battery lifetime, taking into consideration that the implanted battery usually lasts 3 years, and considering that 3 years is approximately 1,000 days, this means that the extra 1/1000 power dissipated in the parallel resistor 132*a* would decrease the battery lifetime from 3 years to a lifetime of 2 years, 11 months and 30 days (instead of 31 days), a perfectly acceptable degradation.

If 132*d* is also 1 M-Ohm, the parallel combined resistance of 132*a* and 132*d* is R-par=500 Ohms, the total "lost" power would be 1/500 of the total, and the total average lifetime of the battery would decrease from a typical 3 years to 2 years, 11 months and 29 days, still very acceptable. These are approximate values for the DBS case, other stimulating devices have similar parameters, and the invention is not bound to work only with these values, as will be appreciated by persons with skills in the art of electronics. Moreover, the value of 132*a* and 132*d* can be different than 1 M-Ohm, as needed for each case, this particular value of 1 M-Ohm being an exemplary case only, not intended to limit our invention.

The switches 130*a* and 130*b* should be as close as possible to the stimulating device 120, which, in the DBS case of the main embodiment, indicates that 130*a* and *b* should preferentially be at the top of the skull, and switches 130*c* and 130*d* should be as close as possible to the battery pack/electronics controlling unit 110, which, in the normal arrangement for DBS means that 130*c* and *d* should be, in the main embodiment, in the chest, just at the exit of the box which contains the battery and the electronics controlling unit.

To turn switches 130 off, the battery pack/electronics control package in 110 turns off, upon telemetry command, switches 130*c* and 130*d*, which in turns automatically starves 130*a* and 130*b* of power, which causes these latter to go into the off state too (assuming that they are of the normally-open type switches). After the MRI session is finished, to turn the stimulating device on again the telemetry control commands the control package in 110 to turn power on for 130*c* and 130*d*, which either automatically, or after another command, turns on the two switches close to 120: 130*a* and 130*b*, after what the electrical stimulating device is ready for operation again.

In the main embodiment, switches 130 (*a, b, c* and *d*) are semiconductor switches, as a bipolar or a FET transistor, which uses less space in the implanted device, which must by necessity be small, but semiconductor switches is not a restriction to our invention, because any other type of switch that can be manufactured on the appropriate size and with bio-compatible materials is within the scope of the invention. The necessary electronics, as transistors, etc., easily fit in the space. In particular, switches 130*c* and 130*d*, which are located near the battery pack/electronics (110) can easily be other technology, as mechanical switches, etc., for robustness, given that they can be inside or at the exit port of the battery 110, with more space available.

It will not escape the persons with knowledge in the art of electronics that the same principles apply to other electrical stimulation, as heart stimulation (heart pacemakers), neural stimulators (as for pain control), physiological electrical stimulators (as for bowel movement control, bladder control, etc.), and devices to cause muscle contraction, as in artificial limbs, etc. all of which causes problems with MRI imaging because all of them needs a relatively long wire, which acts as an antenna for the MRI RF radiation.

Detailed Description for General Background Readers.

Before we describe our invention to the readers that are familiar with the medical aspects of the invention but not familiar with the electronics aspects of it, we want to remind the readers that the devices used in current art, whether used for DBS, stimulation for epilepsy or other neurological malfunctions, heart pacemaking, spinal stimulation, etc. generally contain a sophisticated electronics circuit inside the same box that houses the battery pack (110). This electronics circuit is capable of adjusting the parameters of the electrical stimulation upon command send by telemetry (action at a distance, as radio waves). As used here, the terms radio wave and radiofrequency (RF) apply to frequencies starting at the low end of the AM range (650 kHz) going to at least the upper end of FM and TV frequencies, some few hundreds MHz or more. THz is generally not considered RF anymore, but microwave. For DBS, which is the example used for the main embodiment, the controlling circuits can adjust the stimulating voltage (or current), the pulse frequency and duration, and more. Our device makes use of some extra commands to be added to this existing set in the current art. It should therefore be clear to persons without electronics experience that the possibility of turning on/off the switches 130 (*a*, *b*, *c* and *d*) is a simple extension of current art.

One of the main uses of our invention is for patients with implanted devices which need to have an MRI image (magnetic resonance image). MRI is a modality of imaging in which the protons, mostly in hydrogen are the major responsible for the imaging signal. It is carried or produced placing the object to be imaged inside a strong magnetic field then directing RF radiation to it and measuring how much is absorbed and transmitted as a function of the magnetic field.

During MRI imaging the patient is put inside a strong and homogeneous magnet field, over which there is a slowly space varying magnetic field, and to an electromagnetic (EM) wave of a frequency on the order of 50 MHz, the actual value depending on the strength of the magnetic field. From now on we will refer to this as the RF field or as the 50 MHz wave, though 50 is only an approximate value. The 50 MHz frequency used for MRI is similar in value to the frequency that is used for communications, and is approximately half the frequency used for FM and traditional TV transmission. FM radio reception is affected by the passage of people in front of the radio (if the radio is using its own antenna, and not an external antenna), a fact that can easily be observed walking in front of an inexpensive FM radio receiver, as a bedside clock-radio, which works around 100 MHZ. This signal variation indicates that the FM frequency is capable of interacting with the human body—else there would be no change due to the appearance of a human near the radio; AM does not change as one walks around the radio, because our bodies do not interact with the frequency used for AM, which is around 1 MHz. MRI uses a slightly lower frequency than FM, that is also capable of interacting with the human body. By controlling this EM wave and measuring it after it interacts with the patient, that is, how much of it is absorbed, an image of the atoms inside the body, according to each atom's environment (or the cell structure), can me constructed. Since different tissues have different combinations of atoms and different environment around the same atom, the effect of each tissue on the EM wave is different and measuring this slight changes an image can be made. The EM wave in itself causes no harm to the patient, as it is of a frequency similar to the waves used in communications, a little lower in frequency than the frequency used for FM radio. Some fire, police and other similar services use frequencies near the frequencies used by MRI, at 30 MHz (VHF low), but this information is put here only for completeness, and its accuracy and completeness should not be considered against our invention, because it is independent of our invention and is only included for general understanding of radio frequency EM waves.

The patient undergoing the imaging cannot wear any ferromagnetic metal as iron, because these would be attracted by the strong magnetic field. Any other non-magnetic metal, as copper, aluminum, titanium, even if it is not attracted by the strong magnetic field, causes another adverse effect, as it functions as an antenna for the RF radio frequency wave used for the imaging. The long wire, acting as an antenna, does the same job as an ordinary radio antenna, capturing the radio waves existing in its environment. It happens that metals are far more effective in absorbing electromagnetic waves than human tissues, this being why antennas are usually made with metallic wires, and consequently most of the 50 MHz power used for the image is absorbed by the wires from the battery pack/electronics to the implanted device. Given that the imaging 50 MHz power is very large, the induced voltage and current in the wires can be enough to either destroy the battery pack/electronics or else to heat up the device enough to cause tissue damage. In other words, since the MRI imaging machine bombard the patient with strong, powerful radio frequency waves, as needed for a better imaging, it follows that stronger currents can appear in the wires. This is similar to having a radio near the transmitting antenna and far from it, an effect that one can see driving away from a city: eventually the signal fades away, because the signal strength becomes too low to be captured, the induced voltage too low, or conversely, eventually a station appears on the radio as one approaches a city, because the signal increases in intensity, the induced voltage in the antenna increases its value. It follows that DBS implanted patients may be subjected to induced voltages, and then to the induced currents caused by the induced voltage, in the long wire that runs under the skin from the battery and electronics 110, usually implanted in his/her chest, up and along the neck to the top of his/her skull then down again to the base of the brain inside the skull. Indeed, this is a several feet long wire, which acts as a good antenna for the approximately 50 MHz frequency waves used in MRI imaging. It happens that the radio frequency waves used in imaging are quite powerful, as the requirement is to interact with weakly interacting body molecules, which in turn means that the radio waves induced in the wire running under the skin may deposit uncomfortably large electrical energy, with the potential of causing heat, including in the brain. The problem of induced radio waves EM energy (electromagnetic energy) is not present in normal situations as the patient walks around town, because the normal energy level of the existing radio waves is quite low. It is only the concentration of radio EM energy inside the confined space of the MRI device that can be potentially dangerous. As an exemplary situation we can mention the production of light by fluorescent lamps just standing alone in the air but near a powerful radio transmitting antenna; the high EM fields existing in the close vicinity of the transmitting antenna is enough to cause the fluorescent lamp to produce light without the normal connection with the standard electrical power. A coil near a high-voltage transmission line is able to power some devices, a practice that found its way to the legislature, laws having been passed to forbid the practice because it is a way to capture the electrical energy from the air without paying for it. Analogously to the car approaching and receding a town, in principle one can do the same capture of the electrical energy at any home in town, but in town the 60 Hz wave is lower voltage, too weak to be practical to capture it from the air.

Regarding the total power radiated by the RF imaging coils, it depends on the particular MRI system that is used, but it can easily be around 50 ordinary pressing irons set for full heat—quite a lot of heat indeed!

It is not possible to prevent the induction of EM waves in the wires. Shortening the wires would improve the situation, because the energy induced is proportional to the length of it, among other factors, which could be achieved placing the battery and controlling electronics in the head, nearer to the point of stimulation. But other limitations, among them space in the head, prevent, or make it difficult, to lodge the battery and electronics in the head. In other situations, as heart pacemaker, for example, the points of insertion of the wire for the heart pacemaker, which typically is in the artery/vein near the clavicle also determine a relatively long wire for heart pacemaker too. So far a solution for the length of the wire has not been found and a long wire inevitably captures more EM waves. This has been the conundrum faced by physicians that need MRI images of patients implanted with DBS devices. Our invention seeks to ameliorate this problem of EM waves induced in the long wires that lead from the battery located in the chest to the DBS electrodes 120 implanted in the brain.

It is not possible to prevent the EM induction (electromagnetic induction, the antenna effect, so to say) in the wires, so it is necessary to accept that electric energy will be induced into and then run through the wires when a wearer of electrical implanted devices is undergoing MRI, or otherwise is near any high power EM radiation. Our invention discloses the use of switches that can be closed or opened under the control of the electronics in the battery pack/electronics box 110, which can interrupt the current flow along the wires running from the battery pack to the brain, as in FIGS. 1a and 1b. Just opening the circuit would work, but a safety device is added to our invention, because the possibility that the EM wave induced on the wires could rise the electric potential (the voltage) on the switches, enough to cause them to arc (that is, for a spark to jump across the contacts and the switch going into conducting mode, even if only temporarily). To forestall this electrical energy accumulation on the switches 130, our invention also discloses a closed loop that is used to dissipate the energy induced on it, as described in the sequel. FIG. 1a and 1b display the two situations. The wires running from the battery 110 to the stimulating electrode 120 carry the stimulation signal from the battery pack/controlling electronics 110 to the brain, and 130a, 130b, 130c, and 130d can be closed or opened by telemetry or some other action-at-a-distance, to close or open the electrical path from the connecting wire to the battery pack 110 and to the stimulating electrode 120. The resistors 132a and 132d are also part of the circuit. The resistance of 132a and 132d are of such a value that it is far more difficult for the stimulating current signal sent by 110 to go through them then to go through the stimulating device 120. In our main embodiment we disclose a value of 1000 larger electrical resistance for 132a/132d than for the stimulating device 120. The typical resistance of a DBS-type 120, as used in current art, is around 1 k-Ohms, so 132a and 132d are 1000 k-Ohms=1 M-Ohms resistances. The equation that describes the power usage by resistive electrical devices is the Joule's law, which says that for a fixed electric potential (voltage) the power used is inversely proportional to the resistance, as 1000 times higher resistance, 1000 times less power. Consequently the fixed resistors 132a and 132d use $1/1{,}000 = 0.1\%$ of the total power delivered by the battery, a very small amount of the total power delivered by the 110. Battery lifetime is important for implanted devices, because when the battery runs out, another small surgery needs to be performed to change it; a small surgery to change a box implanted just under the skin, but a surgery nonetheless. Assuming a lifetime of 3 years for the battery, which is typical, and considering that 3 years is approximately 1,000 days, the addition of the 2 resistors, each using $1/1000$ of the power used by the stimulating device 120, subtracts 2 days of operation (one for each resistor), therefore decreasing the total lifetime of the battery from 3 years to 2 years, 11 months and 29 days (on a 31 days month)—a very negligible and eminently acceptable decrease in battery lifetime.

Operation of the Invention

Operation of the Invention for Electrical Engineers.

In the main embodiment of our invention, during normal operation, switches 130 (a, b, c, and d) are set to the conductive, or closed state (see FIG. 1a). In this state the main path from the electrical power source to the stimulating device is the normal path offered by the wires that run through 1d-1a and 1b-1c. Resistors 132a and 132d are in parallel with the circuit of interest (120) but their values, being as it is suggested, 1,000 larger than the device impedance along implanted stimulating device 120, represents only a minimal perturbation of the system that can safely be disregarded—at least as far as energy drain is concerned. The electrical power source is usually a battery, and is a battery for the main embodiment, but not necessarily so. This normal operation is any situation in which the patient is not subjected to very high power of radio frequency. When the patient knows that he/she is going to enter an environment of high power radio frequency, as happens during MRI imaging, the patient him/herself, or a nurse, an M.D., or any other trained personnel, using a telemetry instrument which works together with the implanted electronics in the patient's chest, in a similar way as a remote control of a TV or similar device, sends a command to the electronics in the battery pack/electronics box 110 located in the patient chest to turn off (to the non-conductive or open state) switches 130 (a, b, c and d). Though the main embodiment discloses switches 130 (a, b, c, and d) as under control of the electronics in the box indicated as 110 (several figures), this is not the only possibility, it being also possible that 130 answers to direct commands from the telemetry, or any other combination. In this state, the current that is induced in the connecting wires cannot reach the stimulating device 120 and the battery pack 110 because it is blocked by the interrupted paths at 130. The induced current on the connecting wires would then circulate on the only available closed path, which is through 132a and 132d (FIG. 1b), dissipating the induced EM energy on 132a and 132d.

In the main embodiment switch 130 is controlled by a digital command that is sent by the electronics/control command unit in 110 in the same wire as the power wire, and which is separated from the standard power to 120 by a high frequency pass filter followed by a digital decoder which checks if the digital sequence matches the command to open the switches 130c and 130d. If there is a match the switches are turned off, which starves 130a and 130b of power, which then turns these off too, because in the main embodiment 130 (a, b, c and d) are of the normally open type.

The main embodiment of our invention uses four switches (130a, b, c and d) in line with two wires that run from the battery/electronics box 110 to the stimulating electrodes 120, that is, from the chest to the top of the head and from there into the brain: popularly known as plus and minus, more correctly known as positive and return or positive and ground or better, live and ground or return. In actuality there are several such wires carrying current to the stimulator device, so there exists a plurality of wires wire1, wire2, etc, each of which contains two switches 130a and b, 130c and d, etc. along its length, capable of opening its path. Switches 130, in the main embodiment, are controlled by the controlling electronics, which is, in the main embodiment, packaged with the battery 110 in the patient's chest. The extra wires that connect 132a create a loop to dissipate the energy induced in the wires that lead to the stimulating device 120. The introduction of the closed loop is crucial for the invention, for without it the electric potential difference (often called voltage in US) would increase on the switches 130a, b, etc. by the induced EMF effect, as described by Maxwell's equations, eventually causing arcing, possible destruction of the switches, and potential harm to the patient. From this controlling electronics, which is capable of receiving controlling signals by radio waves or some other type of telemetry, a wire with a command runs to the switches 130a, 130b, etc. In the main embodiment this is the same as the power wire, separated by a high-frequency filter to select the command for 130a, b, etc. The command may be, for example, f=100 kHz to turn switch on (completing the connection), and 10 kHz to turn the switch off (disconnecting the connection), and the switches should latch once set in any state. It is also possible to have separate command wires for this control, but the main embodiment uses the same as the power wire to save space in an implanted device. In the normal situation for brain stimulation, that is, current running through 130a, b, c and d, to the stimulating electrodes in the brain 120, CW1 is set to the on (or conducting state), while during MRI imaging CW1 is set to the off state. In the former situation (stimulation working) almost all the electrical current, as set by the controlling electronics in the battery pack/electronics control 110 in the patient chest, is directed to the stimulating electrode 120 in the brain, while in the latter situation (during MRI imaging) there is no possible electrical current path to the implanted electrodes, while an alternative path is available to dissipate the energy in the resistances along the loop 1a-1b-1c-1d-1a through dumping resistors 132a and 132d.

Operation of the Invention for General Background Readers.

Varying electromagnetic fields always induce currents on wires which are in their space. This is why antennas pick up radio signals, and why transformers work as they do. This is an unavoidable result. Therefore, the wires that carry the power or other electrical signals to the stimulating device are certain to "absorb" electrical energy from the approximately 50 MHz imaging radio frequency wave used for the MRI imaging. This "absorbed", or induced electric current, is capable to cause harm to the wearer of implanted electrical devices, because the imaging radio frequency wave carry power equivalent to 20 or more pressing irons (20 kW or more), which is a lot of heat. Since this induced power cannot be prevented, our invention discloses a set of switches 130 (a, b, c, and d) to disconnect the battery+electronics in box 110, and the stimulating device 120, of the wires that connect them. In the main embodiment the switches 130 (a, b, c, and d) are semiconductor switches. 130 (a, b, c, and d) etc. are controlled by signals sent over the power wires, blocked from the switches by a high-frequency passing filter, that is a frequency filter that only allows high frequencies to pass, which is able to pass to types of signals, at two different frequencies f1=10 kHz and f2=100 kHz, one to turn 130 on, the other to turn 130 off.

Once 130 is off, the continuous path through the stimulating device 120 and through the battery/electronics box 110 is open (that is, not available to electrical conduction), which causes that the only closed path for current flow is the path that goes through resistors 132a and 132d, which then dumps the induced EM radiofrequency induced on the connecting wires.

Without the alternative path through 132a and 132d, the electric potential (known as voltage in US) would increase with the possibility of arcing and destruction of switches 130, besides opening 120 and 110 to destruction by the high current induced by the induced radio frequency signal. With the available path through 132a and 132d, these act as energy dump, dissipating the energy induced in the wires that are part of the implanted device.

Description and Operation of Alternative Embodiments

Several alternative embodiments are possible. For example, it is possible to have one single switch in each stimulating wire, say near the skull, 130a, omitting the second switch 130b, on the return wire, because once the path is broken no current can flow through stimulating electrodes 120. Likewise for the battery pack/electronic circuit, it is possible to omit 130d, keeping only 130c, for the same reason. Redundancy may be preferable to offer more protection, this being why the main embodiment contains redundancy, a common practice in all branches of engineering, but redundancy is not necessary for the operation of the basic principle of this invention, which is to break the path for induced current while opening an alternative path to dissipate the energy induced by the high frequency external EM field.

Another alternative embodiment is to use filters F1a, F1b, etc and F2a, F2d, etc., passive or active filters, in lieu of the switches 130a, 130b, etc. and in line with 132a, 132d etc., or in lieu of these. The word "filter" is used in the art of electronics engineering to mean "frequency selective device", devices that provide an easy flow for some frequencies and a difficult flow for other frequencies.

This option would obviate the necessity of switches to open the circuit leading to the stimulating device 120 and the battery/electronics pack 110. This option would use low-pass filters (filters that pass low frequencies only) to close the path for the RF higher frequencies induced by the MRI equipment, to both the stimulating device 120 and the battery/electronics pack 110. A low-pass filter (that allows passage of only low frequencies) is a permanently blocking switch 130 for the higher frequency induced currents that cause the damage during MRI. Likewise, a high-frequency pass filter is a constantly unimpeded path to allow the flow of the induced RF (high frequency, around 50 MHz), to flow through the loop composed of resistors 132a and 132d. For example, a low-pass filter F1 could permanently connect the wires that connect 110 to 120 in place of the switches 130 (a, b, c and d), this filter designed to have low impedance Z1-low (low resistance, or conductive state) to the low frequency used by the stimulation signal (usually around 10 kHz, but the exact value is not part of this invention but it is old art, as practiced by neurologists), while having high impedance Z1-high (high resistance, or non-conductive state) for the high frequency characteristic of the induced radio frequency signals, e.g., used by imaging MRI, which is of the order of 50 MHz, depending on the static magnetic field, which is typically of the order of 2 to 5 Tesla. Such a filter F1, in the positions where 130 are located in the main embodiment, would allow the desired stimulating frequency (=~10 kHz) to flow into the neuron stimulator 120, while permanently blocking most of the energy at the much higher frequencies (=~50 MHz) created by MRI imaging systems. Such an alternative embodiment may also have a different set of filters F2 (high-pass filters, that pass the high frequencies) could be added in series with 132a and 132d, such that Z1-low<<132a<<Z2-low (at low frequencies)
Z2-high<<132a<<Z1-high (at high frequencies), Where low frequencies above means around 10 kHz, which corresponds to the 200 Hz stimulating signal of 100 microsecond pulsewidth, corresponding to a 10 kHz frequency, and high frequencies means 50 MHz, which are the stimulating frequencies and the imaging frequencies, respectively. Note here that the actual stimulating frequency used by existing art is 200 Hz (200 square pulses per second), but with 100 microsecond wide pulses, which corresponds to a frequency of 10 kHz. It can be proved mathematically that to pass a 100 microsecond pulse every 200 times per second (200 Hz), it takes a filter that is easy for 10 kHz.

In this case the low frequency signal (approximately 10 kHz) would find a much easier path (through Z1-low) to the stimulating electrode 120 than through the alternative parallel path through Z2-low and 132a, while the opposite would happen with the RF high frequency induced signal at approximately 50 MHz by the MRI system, which would find an easier path through 132a and 132d, via Z2, than to the stimulating electrode 120. In this alternative embodiment most of the desired signal would still go to the electrode 120 while most of the undesirable RF signal would still be dissipated in Ra, via Z2, etc, instead of depositing its energy in the electrode 120 or in the battery pack/electronics 110.

It is also possible to have other combinations of frequency filters (usually known in the electronics art simply as filters) and the main embodiment. For example, it is possible to have the main embodiment and filters F2 described above in series with 132a and 132d, with high impedance for low-frequencies (around 10 kHz) and low impedance for high-frequencies (around 50 MHz). Such an addition would make the main embodiment more robust, with less wasted energy on the dumping resistors 132a and 132d.

It is also possible to have some of the switches 130 as described in the main embodiment, while others being substituted by the filters F1 described above, for example, have 130c and 130d (the left side of FIG. 1), substituted by filters F1c and F1d.

Many other combinations are possible, as the persons with skills in the art will see, which are still in the scope of our invention.

Persons with skills in the art of medicine but not in the art of electronics can look at filters as a permanent selective switch that blocks certain signals while allowing other signals to proceed, the selection being made according to the frequencies of the signals. Persons with skills in the art of medicine but not in the art of electronics can appreciate that such a filtering is what occurs in all radio receivers, which separates a station transmitting at a certain frequency from another station transmitting at another different frequency. Frequency filters are common in the art of electronics and are a developed field.

Figure 2A:
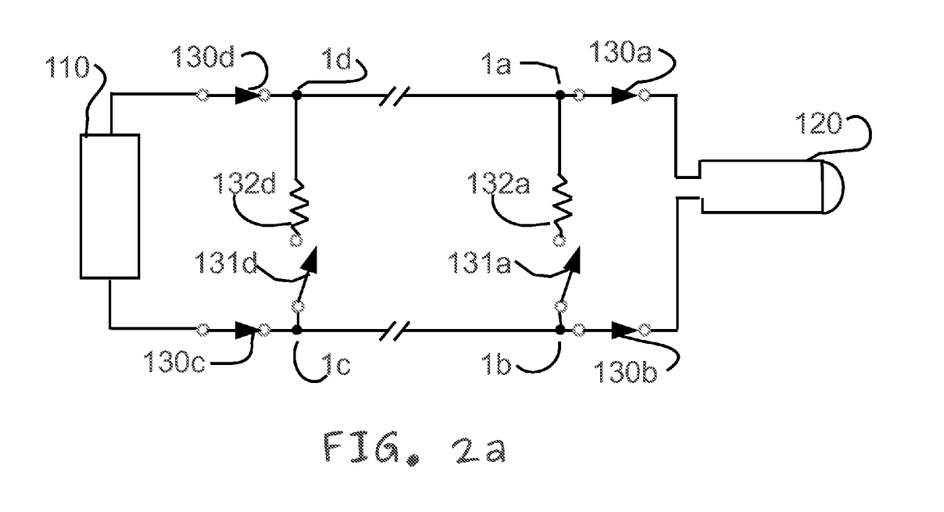
FIG. 2 shows a schematic representation of a variation of the implementation of the main embodiment of this invention.
Figure 2B:
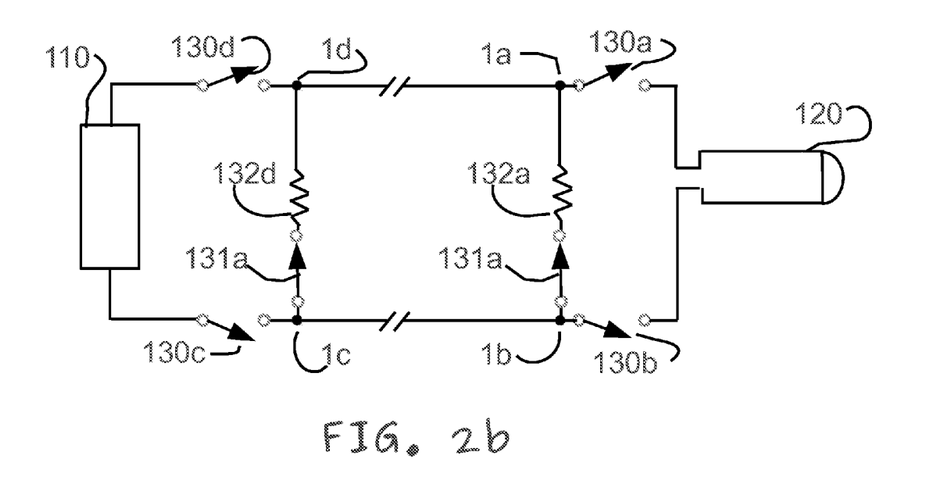

Another possible alternative embodiment shown in FIGS. 2a and 2b, is to use switches 130 as in the main embodiment and switches 131a and 131d, in series with resistors 132a and 132d. This latter switches would be in the on, or conductive state when 130 is in the off, or non-conductive state, and vice-versa. FIG. 2a displays the case where the current flows through the stimulating device (normal use) and FIG. 2b displays the case where the stimulating device is disconnected while the alternative path through resistors 132a and 132d are connected in a closed loop through switches 131a and 131d. During normal stimulation, which is the case all the time except during MRI imaging situations, all 130 are in the on state (conductive state), allowing current to flow through stimulating device 120 and/all 131 are in the off state (non-conductive state), blocking this alternative path through 132a and 132d. Conversely, during MRI imaging, all 130 would be turned, by telemetry, to the off (or non-conductive) state, and all 131 would be turned, by telemetry, to the on (or conductive) state, thereby isolating both the stimulating device 120 and the battery/electronics box 110, while connecting the alternative network a-b-c-d-a, through resistors 132a and 132d, where the induced RF energy is dissipated.

Another possibility is to have filters with impedances Z1 (in the path to 120) and Z2 (in the path of 132a and 132d) as above, and also switches 131 in series with Z2. Such switches 131 would then be of the type normally opened switches (normally not conducting), which would go into the closed state (conducting state) upon receiving a digitally-coded signal, for example, short-short-short-long-long-long-short-short-short, which would open a conductive path to filters Z2 and 132a, 132d, etc. Such a variation would cause a much larger impedance (resistance) to the alternative energy-dumping path through 132a, 132d, etc. when the patient is in the normal state, at which times it would be preferable not to have 132a, 132d, etc.

Several possible alternatives are possible. One such possible variation is that the loop wires, e.g., the wire connecting points a to b, where 132a and 132d are located, are made of such an alloy as to offer a substantially larger resistance per unit length (resistivity), than the total resistance of the loop wire that goes from the battery to the stimulating device. For example, the total resistance of the wire connecting a to b can be 1000 times larger than the total resistance of the stimulating wire that goes from the battery to the stimulating device. Such wire with such a distributed resistance, 1000 times larger than the stimulating wire, would dissipate one thousand times less electrical energy than the stimulating wire, because the power dissipated is, according to Watt's power dissipation equation, P=(delta-V)^2/R.

Another possibility is to have said resistors 132a and 132d connected in cross: 132a connected from point 1a to point 1c and 132d connected from point 1d to point 1b. Such a connection, which would make an "X" in FIG. 1, still keeping the general objective of offering an alternative path to any current induced by RF in the connecting wires.

Another possibility is to have said resistors 132a and 132d connected in parallel with said connecting wires from point 1b to point 1c and said return wire from point 1a to point 1d: 132a connected from point 1a to point 1d and 132d connected from point 1b to point 1c. Such a connection would be in parallel with connecting wires that carry the electrical current from the electrical energy source/electronics circuit to the stimulating electrodes.

Another possibility is to have several power carrying wires at different voltages (or current) levels, which opens the possibility of having different stimulating electrodes at different voltages (or current) levels. In this case each separate power carrying wire has its individual switch 130.

Another possibility is to have a plurality of wires for use as control wires as normally used in digital electronics. These control wires could select one or another possible combination of functions at the stimulating device 120.

Another possibility is to have a plurality of wires for use as address wires, as normally used in digital electronics. These address wires could select one of a plurality of electrodes at the stimulating device 120. In this case the stimulating device has the appropriate decoder associated with each stimulating electrode (or pad), which is selected or deselected according to its own address, using the normal practices of digital addressing.

Another possibility is to have the plurality of control wires and address wires as a single wire which convey the information for the stimulating device 120 in a serial fashion, as, for example, USB serial connection. In this case the minimum wire number is one (plus return wire which may be common with all other wires due to the device working at low frequencies). In this case there exists a serial to parallel converter in the stimulating device 120.

Figure 3:
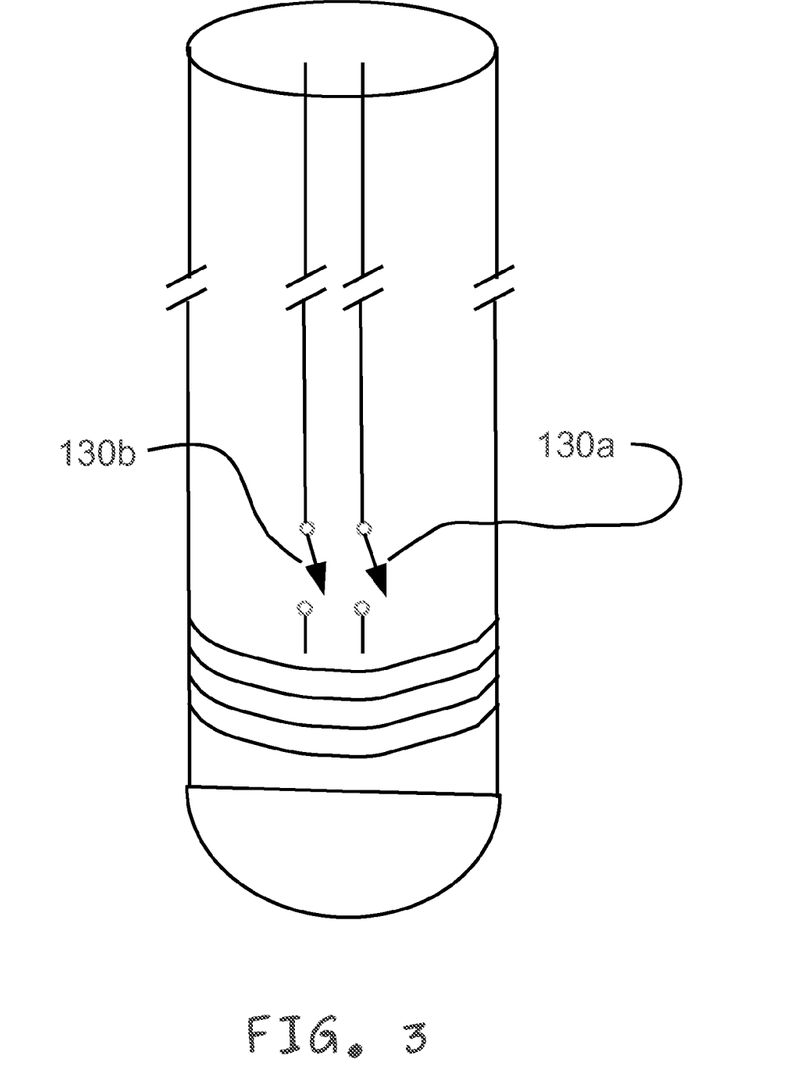
FIG. 3 shows a possible variation of the main embodiment with extra switches 130*a* and 130*b* inside the picafina of our invention, just before the beginning of the stimulating electrodes.

Another possibility is to have switches 130 inside the stimulating device instead of outside it as in FIG. 1. This possibility is shown in FIG. 3.

Another possibility is to have one or a plurality of dedicated wires (not shown) to control switches 130 and 131 (and others).

Figure 4:
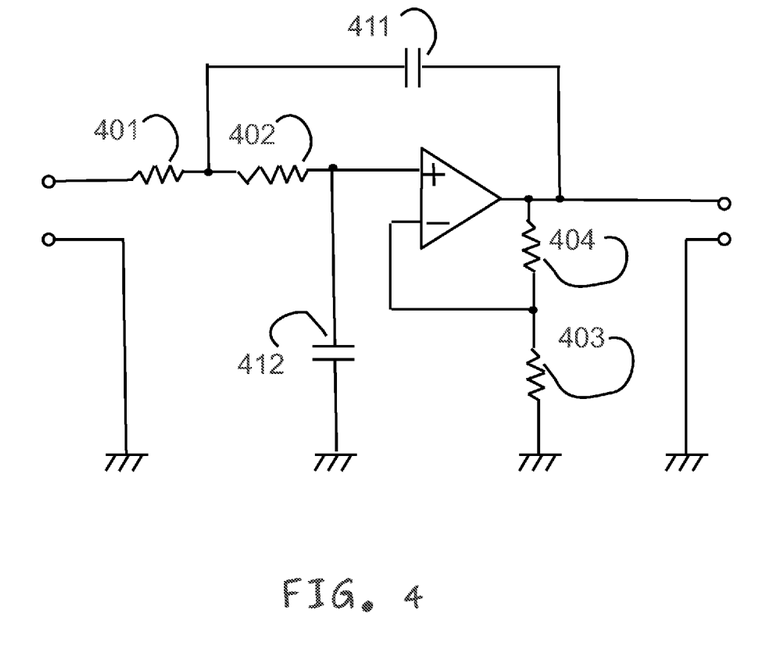
FIG. 4 shows an op-amp based low pass filter of the VCVS variety (Voltage-controlled voltage-source)

Other alternatives that are possible for the VCVS filter displayed in FIG. 4. For example a Chebychev filter is another type of active filter, as are a Sallen-and-Key filter, a Butterworth filter, a Bessel filter, and so on. Indeed, any active filter would do a similar frequency blocking still using small size capacitors. A particular case may be better with a particular active filter, and the difference between any two filters may be larger or smaller, depending on the case, but the particular active filter type is unimportant for this invention but only that it is a frequency selective device.

Another possible alternative for the main embodiment is to have active filters placed at more places along the wires, for example, every 10 cm. along any wire, or any other spacing. Such multiple filters would contribute for the prevention of pulse propagation along the wire on a multiplicative manner, besides preventing any current build-up on the wires. Given that the filters would use power only when activated, which is expected to be rarely, there would be no power disadvantage associated with such a scheme, while offering better filtering and imaging RF blocking.

Another possible alternative for the main embodiment is to have active filters and switches together all the time. In such an alternative embodiment the high frequency induced signal would always see a difficult path to the stimulator 120 and to the battery pack/electronics 110, on top of which the electrical path would be opened (disconnected) during MRI imaging.

Another possible alternative embodiment is for stimulating devices which uses one connecting wire only, using the body of the wearer as a return path. Some stimulating devices are of this type. In this case there exists one wire only, and only 130a and 130c. In this case 132a and 132d connect each wire extremity to the body of the wearer, which forms the return path. As it will be appreciated by electrical engineers, connecting the four switches as said does offer some degree of protection to both the battery pack 110 and the stimulating device 120.

One of the improvements of our invention over prior art electrical stimulating devices, is the introduction of one or several switches, in-line (along the path) of the pertinent wires, which are capable of opening the conductive electrical path on the wires going from the battery pack/electronics located on the chest to the top of the head and implanted electrode, therefore interrupting the path of the radio frequency waves induced by the MRI or other processes. Such switches, which can be located in a plurality of places along the electrical path are controlled by telemetry or some action at a distance, using radio control or the like. These controls, action-at-a-distance can act either on the controlling electronics housed in 110, which would in turn issue the appropriate commands, carried by wires or by radio signals, to the switches, or they can act directly on the switches themselves. Moreover, our invention discloses switches which are capable of being turned on or off, or to direct the electrical current one path or another, or to disconnect the wire altogether, acting upon external commands, which are send by telemetry, using the existing methods of telemetry to control and adjust the prior art devices, many of which are capable of being adjusted to the needs of each patient using an external programmer.

Accordingly, prior to an MRI imaging session, a trained technician, nurse, or medical doctor, can disconnect the normal, low impedance pathway for electrical stimulation, causing that an alternative available circuit containing a network of simple resistors (as 132a, 132d, etc.), or a network of simple resistors and high-pass filters, that is, filters that allow high frequency to pass with little opposition, is available for the unavoidable induced RF to dissipate the induced energy in the wires that connect the electrical stimulation device. The high-pass filters can be made with either passive or active devices.

An active filter (op-amp based) is better than a passive (RC, RLC) filter because it offers sharper transitions from passing-to-blocking frequencies. Active filters rely on an external power supply, which in most cases is no problem, but in the case of an implanted device, which runs on the power of an implanted battery, which needs surgery for replacement, the energy used by an active filter is a serious disadvantage. Indeed, given that every electrical engineer is aware of the superiority of active filters over passive ones, the inventors suggest, but this is not known for sure, and should not therefore be used against the invention, that the use of active filters were never introduced before due to their power consumption. This invention discloses a solution to this problem, as seen in the sequel. Moreover, in the majority of cases, such an active filter consumes power for no reason, because it is only needed if the patient undergoes an MRI imaging procedure, which happens only infrequently. Besides, even when a particular patient is subjected to an MRI procedure, the imaging procedure lasts for less than one hour, an insignificant time when compared with the years during which the active filter consumes the precious battery power. The solution we propose is to have one or a series of active filters, which are powered on demand by the standard telemetry (radio commands) sent to the battery/electronics pack; when not undergoing MRI imaging, or any other potentially EM exposure, the active filter is disconnected from the circuit, therefore not using the precious battery power. Immediately before an MRI imaging, the active filter is turned on and connected to the circuit as needed, providing a better blocking filter for the EM RF frequency used by the imaging procedure, offering a better protection than a passive RC or RLC filter would.

Another advantage of a active filter is their sizes. Active filters can be designed to work with small valued capacitors. Also op-amps can mimic the electrical characteristics of inductors, effectively creating an inductor-in-a-chip, which is of a size compatible with an implanted device.

Description of Alternative Embodiments for Non-Engineers.

It is not possible to prevent the EM induction (electromagnetic induction, the antenna effect, so to say) in the wires, so it is necessary to accept that electric energy will enter (penetrate) the wires of the electrical stimulating devices, then travel to the stimulating device 120 and battery pack/electronics 110. Our invention discloses the use of selective switches that may block the electrical current, and filters that substantially blocks the propagation of such electric energy along the wires, and also of filters and alternative routes (networks) that bypass the deposited electric energy to less harmful locations in the body, as muscles. Our invention also discloses the introduction of switches 130 and 131 (a, b, c, etc.) located at strategic points in the circuit so as to eliminate or at least to minimize the damage caused by such induced currents. Induced currents can occur during MRI imaging and also in any other situation where the patient is exposed to electromagnetic radiation, the power of it increasing the danger of the consequent harm to the patient.

One possible technology to make electrical filters to selective block the flow of some currents but not others, is the use of active filters, which are built with amplifiers known as op-amps. The op-amps themselves drain electric power, which is at a premium in an implanted device whose battery requires surgery for replacement. This power drain on the battery, if continuous, would put the use of active filters or any other active circuit out of the realm of the possibility. Our invention discloses a system of switches that turns the active circuits off unless they are needed, that is, unless the patient is entering a situation that requires high frequency protection. Our invention discloses a system that drains power for its operation only when the patient needs the protection from radio frequency EM radiation from magnetic resonance imaging (MRI).

FIG. 3 shows an active filter constructed with an op-amp (operational amplifier) of the VCVS variety. Op-amps are fully functional amplifiers built in a chip, sometimes several in a chip, offering high gain, with which it is possible to built a variety of circuits, including frequency filtering circuits, or circuits that oppose the flow of AC at some frequencies only, while allowing AC current at other frequencies to pass. Active filters are more selective than passive filters, the former using external electric power to function, the latter using no external power to function. The former is based on transistors or their equivalents, the latter is based on resistors, capacitors and coils. The actual op-amp is very small; even with ancient, 80's technology, a 741 op-amp with 24 transistors, comfortably fits on a pin head, that is, on an area 500 micrometers in side. The full circuit, including the resistors and capacitors, can be made together in an area that is barely visible to the human eye with 80's technology, or to an area or 5 by 5 micrometers with Petium 4 manufacturing technology of 2004. Note that 5 by 5 micrometers is well smaller than what is visible to the naked eye. It is therefore perfectly feasible to have some such op-amp based circuits spaced along the connecting wire, such filters being so designed as to substantially block the 50 or so MHz AC induced by the MRI imaging system.

CONCLUSION, RAMIFICATIONS, AND SCOPE OF INVENTION

In the main embodiment and in its variations disclosed, the switches in line with the stimulation carrying wires are placed before, or outside the stimulating electrodes that reside in the brain. This is not necessary, it being also possible to have some interrupting switches in the stimulating electrode too.

The electronic switches can be implemented from transistors, as bipolar transistors, FETs, etc., or a specially designed commercial switch as the Fairchild Semiconductor FSA2259 (Low-Voltage 0.8 Ohm Dual-SPDT Analog Switch) or any other standard, off-the-shelf commercially available semiconductor switch, offered by many semiconductor company. Semiconductor switch is an established branch of electronics which is not part of this invention. If a commercial switch is used, it is understood that what would be used is the die, not the packaged chip, which is much too large for the application in question.

The switches can be closed or opened from a distance. The switches 130, 131, etc. can be controlled either by the electronics circuitry together with the battery pack or by direct telemetry, that is, from an outside command via radio, or infrared, etc. signals. The controlling commands can be digital or analog, without changing the scope of the invention.

The switches of the main embodiment and its variations can be operated by radio command, as disclosed in the main embodiment but also by other types of telemetry, as infrared, ultrasound, etc., as is obvious to the persons familiar with the art. Radio command was used only as a possible example, it not being intended to be a limitation of the invention.

The extra wires (wires WireControl1 and WireControl2, not shown) to control the switches 130 and 131 can be replaced by a digital code which can be send by the existing wires that send the pulses to the implant. This is similar to a radio controlled garage door opener, some of which send a particular digital sequence which is recognized by the garage door opener mechanism that acts accordingly. In this case the digital signal is sent by the wire, the same wire that carries the electrical stimulation pulse. It is also possible that instead of the switches be under control of the battery pack/electronics box, they are under direct control of an external device, in this case much like a garage door opener. In either case, the switches would contain a digital signal decoder to detect the digital signal with the instruction to open or to close each switch. These signals are common electronics circuits, widely used by many common devices, and are not part of this invention, which simply can be made with any of the existing prior art.

What is claimed is:

1. A system for mitigating the effects of an electromagnetic energy induction device on an implanted electrical stimulating device, the system comprising:
 a first electrical network comprising one or more electrodes of a plurality of electrodes implanted at a first location;
 an electrical energy storage means and an electronics controlling unit implanted at a second location;
 an electrical conducting means, connecting the one or more electrodes of a plurality of electrodes at the first location to the electrical energy storage means and the electronics controlling unit at the second location;
 wherein a second electrical network comprising either a first plurality of electrical switches and a second plurality of electrical switches or a first plurality of electrical switches, a second plurality of electrical switches and a third plurality of electrical switches creating a closed circuit connecting the electrical conducting means to one or more energy dissipating devices of a plurality of energy dissipation devices.

2. The system of claim 1, wherein the electrical energy storage means and the electronics controlling unit are implanted at separate locations.

3. The system of claim 1, wherein a first plurality of electric switches are configured to provide electrical continuity for electrical current flow, or to interrupt the one or more electrodes of a electrical current flow between the one or more electrodes of a plurality of electrodes and the electrical conducting means, and the second plurality of electric switches configured to provide electrical continuity for electrical current flow, or to interrupt the electrical current flow between the electric storage means and the controlling electronics unit and the electrical conducting means.

4. The system of claim 3, wherein the continuity states of the first plurality of electric switches and the second plurality of electric switches are controlled by a human operator via telemetry.

5. The system of claim 3, wherein the continuity states of the first plurality of electric switches and the second plurality of electric switches are automatically selected by the controlling electronics.

6. The system of claim 3, wherein the first plurality of electrical switches and the second plurality of electric switches are semiconductor switches.

7. The system of claim 1, wherein the third plurality of electric switches is configured to provide electrical continuity for electrical current flow, or to interrupt the electrical current flow between the second electric network from the electrical conducting means.

8. The system of claim 7, wherein the continuity states of the third plurality of electric switches are controlled by a human operator via telemetry.

9. The system of claim 7, wherein the continuity states of the third plurality of electric switches are automatically selected by the controlling electronics.

10. The system of claim 7, wherein the third plurality of electric switches are semiconductor switches.

11. The system of claim 1, wherein the energy dissipation devices are resistors.

12. The system of claim 1, wherein the energy dissipation devices are inductors.

13. The system of claim 1, further comprising capacitors connected in series with the energy dissipation devices, the capacitors being configured to provide smaller impedance to the electromagnetic energy induction devices in the system than the impedance provided to the one or more electrodes of a plurality of the electrodes.

14. The system of claim 1, further comprising capacitors connected in series with the energy dissipation devices, the capacitors being configured to provide smaller impedance to the electromagnetic energy induction devices in the system than the impedance provided to the electric energy storage means and the electronics controlling unit.

15. The system of claim 1, wherein the electromagnetic energy induction device is an MRI system.

16. The system of claim 1, wherein the one or more electrodes of a plurality of electrodes are configured to provide electrical stimulation in a brain.

17. The system of claim 1, wherein the one or more electrodes of a plurality of electrodes are configured to provide electrical stimulation in a heart.

18. The system of claim 1, wherein the one or more electrodes of a plurality of electrodes are configured to provide electrical stimulation in a stomach.

* * * * *